(12) United States Patent
Zinger et al.

(10) Patent No.: US 8,016,809 B2
(45) Date of Patent: Sep. 13, 2011

(54) LIQUID DRUG DELIVERY DEVICES FOR USE WITH SYRINGES WITH WIDENED DISTAL TIPS

(75) Inventors: Freddy Zinger, Ra'anana (IL); Niv Ben Shalom, Netanya (IL)

(73) Assignee: MEDIMOP Medical Projects Ltd., Ra'anana (IL)

( * ) Notice: Subject to any disclaimer, the term of this patent is extended or adjusted under 35 U.S.C. 154(b) by 42 days.

(21) Appl. No.: 12/679,676

(22) PCT Filed: Sep. 24, 2008

(86) PCT No.: PCT/IL2008/001278
§ 371 (c)(1),
(2), (4) Date: Mar. 24, 2010

(87) PCT Pub. No.: WO2009/040804
PCT Pub. Date: Apr. 2, 2009

(65) Prior Publication Data
US 2010/0198148 A1      Aug. 5, 2010

(30) Foreign Application Priority Data
Sep. 25, 2007   (IL) .......................................... 186,290

(51) Int. Cl.
*A61M 5/32*          (2006.01)
(52) U.S. Cl. ........................ 604/414; 604/411
(58) Field of Classification Search .................. 604/126, 604/190, 403, 405, 406, 411–415, 537, 539; D24/129, 130; 215/247, 249
See application file for complete search history.

(56) References Cited

U.S. PATENT DOCUMENTS

| | | | |
|---|---|---|---|
| 62,333 | A | 2/1867 | Holl |
| 1,704,817 | A | 3/1929 | Ayers |
| 1,930,944 | A | 10/1933 | Schmitz, Jr. |
| 2,326,490 | A | 8/1943 | Perelson |
| 2,931,668 | A | 4/1960 | Baley |

(Continued)

FOREIGN PATENT DOCUMENTS

DE        1913926 A1      9/1970

(Continued)

OTHER PUBLICATIONS

Office Action issued Nov. 12, 2010 in U.S. Appl. No. 29/334,697.

(Continued)

*Primary Examiner* — Nicholas D Lucchesi
*Assistant Examiner* — Victoria P Campbell
(74) *Attorney, Agent, or Firm* — Panitch Schwarze Belisario & Nadel LLP

(57) ABSTRACT

Liquid drug delivery device includes a housing with a syringe port for sealingly receiving a syringe having a syringe tip ending at a widened distal tip, a vial adapter port with a vial adapter for snap fit receiving a vial, and a drug administration port for administering a liquid drug. The vial adapter is intended to be rotationally detached after a mixing procedure for discarding together with a spent vial. The syringe port additionally includes a single use locking mechanism for securing the syringe to preclude inadvertent syringe detachment under normal use including agitation for reconstitution purposes. The drug administration port has a distal tip preferably similar to a syringe's widened distal tip for the same purpose of preventing conventional needles with a female Luer connector being slidingly mounted thereon.

7 Claims, 8 Drawing Sheets

U.S. PATENT DOCUMENTS

| | | |
|---|---|---|
| 2,968,497 A | 1/1961 | Treleman |
| 3,059,643 A | 10/1962 | Barton |
| D198,499 S | 6/1964 | Harautuneian |
| 3,484,849 A | 12/1969 | Huebner et al. |
| 3,618,637 A | 11/1971 | Santomieri |
| 3,757,981 A | 9/1973 | Harris, Sr. et al. |
| 3,826,261 A | 7/1974 | Killinger |
| 3,885,607 A | 5/1975 | Peltier |
| 3,957,052 A | 5/1976 | Topham |
| 3,977,555 A | 8/1976 | Larson |
| 3,993,063 A | 11/1976 | Larrabee |
| 4,020,839 A | 5/1977 | Klapp |
| 4,051,852 A | 10/1977 | Villari |
| 4,109,670 A | 8/1978 | Slagel |
| 4,187,848 A | 2/1980 | Taylor |
| 4,210,173 A | 7/1980 | Choksi et al. |
| D257,286 S | 10/1980 | Folkman |
| 4,253,501 A | 3/1981 | Ogle |
| 4,296,786 A | 10/1981 | Brignola |
| 4,314,586 A | 2/1982 | Folkman |
| D267,199 S | 12/1982 | Koenig |
| D271,421 S | 11/1983 | Fetterman |
| 4,434,823 A | 3/1984 | Hudspith |
| 4,475,915 A | 10/1984 | Sloane |
| 4,493,348 A | 1/1985 | Lemmons |
| D280,018 S | 8/1985 | Scott |
| 4,532,969 A | 8/1985 | Kwaan |
| 4,564,054 A | 1/1986 | Gustavsson |
| 4,576,211 A | 3/1986 | Valentini et al. |
| 4,588,396 A | 5/1986 | Stroebel et al. |
| 4,588,403 A | 5/1986 | Weiss et al. |
| D284,603 S | 7/1986 | Loignon |
| 4,604,093 A | 8/1986 | Brown et al. |
| 4,607,671 A | 8/1986 | Aalto et al. |
| 4,614,437 A | 9/1986 | Buehler |
| 4,638,975 A | 1/1987 | Iuchi et al. |
| 4,639,019 A | 1/1987 | Mittleman |
| 4,667,927 A | 5/1987 | Oscarsson |
| 4,676,530 A | 6/1987 | Nordgren et al. |
| 4,697,622 A | 10/1987 | Swift et al. |
| 4,721,133 A | 1/1988 | Sundblom |
| 4,729,401 A | 3/1988 | Raines |
| 4,743,229 A | 5/1988 | Chu |
| 4,743,243 A | 5/1988 | Vaillancourt |
| 4,758,235 A | 7/1988 | Tu |
| 4,759,756 A | 7/1988 | Forman et al. |
| 4,778,447 A | 10/1988 | Velde et al. |
| 4,787,898 A | 11/1988 | Raines |
| 4,834,152 A | 5/1989 | Howson et al. |
| 4,865,592 A | 9/1989 | Rycroft |
| 4,909,290 A | 3/1990 | Coccia |
| 4,967,797 A | 11/1990 | Manska |
| D314,050 S | 1/1991 | Sone |
| 4,997,430 A | 3/1991 | Van der Heiden et al. |
| 5,035,686 A | 7/1991 | Crittenden et al. |
| 5,045,066 A | 9/1991 | Scheuble et al. |
| 5,049,129 A | 9/1991 | Zdeb et al. |
| 5,053,015 A | 10/1991 | Gross |
| 5,061,248 A | 10/1991 | Sacco |
| 5,088,996 A | 2/1992 | Kopfer et al. |
| 5,096,575 A | 3/1992 | Cosack |
| 5,104,387 A | 4/1992 | Pokorney et al. |
| 5,113,904 A | 5/1992 | Aslanian |
| 5,122,124 A | 6/1992 | Novacek et al. |
| 5,125,908 A | 6/1992 | Cohen |
| 5,171,230 A | 12/1992 | Eland et al. |
| 5,201,705 A | 4/1993 | Berglund et al. |
| 5,201,717 A | 4/1993 | Wyatt et al. |
| 5,203,771 A | 4/1993 | Melker et al. |
| 5,203,775 A | 4/1993 | Frank et al. |
| 5,211,638 A | 5/1993 | Dudar et al. |
| 5,232,109 A | 8/1993 | Tirrell et al. |
| 5,247,972 A | 9/1993 | Tetreault |
| 5,269,768 A | 12/1993 | Cheung |
| 5,270,219 A | 12/1993 | DeCastro et al. |
| 5,279,576 A | 1/1994 | Loo et al. |
| 5,288,290 A | 2/1994 | Brody |
| 5,312,377 A | 5/1994 | Dalton |
| 5,328,474 A | 7/1994 | Raines |
| 5,334,163 A | 8/1994 | Sinnett |
| 5,342,346 A | 8/1994 | Honda et al. |
| 5,344,417 A | 9/1994 | Wadsworth, Jr. |
| 5,350,372 A | 9/1994 | Ikeda et al. |
| 5,364,387 A | 11/1994 | Sweeney |
| 5,374,264 A | 12/1994 | Wadsworth, Jr. |
| 5,385,547 A | 1/1995 | Wong et al. |
| 5,397,303 A * | 3/1995 | Sancoff et al. ............ 604/82 |
| 5,445,630 A | 8/1995 | Richmond |
| 5,464,123 A | 11/1995 | Scarrow |
| 5,466,219 A | 11/1995 | Lynn et al. |
| 5,466,220 A | 11/1995 | Brenneman |
| 5,478,337 A | 12/1995 | Okamoto et al. |
| 5,492,147 A | 2/1996 | Challender et al. |
| 5,505,714 A | 4/1996 | Dassa et al. |
| 5,509,433 A | 4/1996 | Paradis |
| 5,520,659 A | 5/1996 | Hedges |
| 5,526,853 A | 6/1996 | McPhee et al. |
| 5,531,695 A | 7/1996 | Swisher |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley, III et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,641,010 A | 6/1997 | Maier |
| 5,647,845 A | 7/1997 | Haber et al. |
| 5,651,776 A | 7/1997 | Appling et al. |
| 5,653,686 A | 8/1997 | Coulter et al. |
| 5,674,195 A | 10/1997 | Truthan |
| 5,718,346 A | 2/1998 | Weiler |
| D393,722 S | 4/1998 | Fangrow, Jr. et al. |
| 5,738,144 A | 4/1998 | Rogers |
| 5,743,312 A | 4/1998 | Pfeifer et al. |
| 5,746,733 A | 5/1998 | Capaccio et al. |
| 5,755,696 A | 5/1998 | Caizza |
| 5,772,630 A | 6/1998 | Ljungquist |
| 5,772,652 A | 6/1998 | Zielinski |
| RE35,841 E | 7/1998 | Frank et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,893,397 A | 4/1999 | Peterson et al. |
| 5,919,182 A | 7/1999 | Avallone |
| 5,925,029 A * | 7/1999 | Jansen et al. ............ 604/411 |
| 5,944,700 A | 8/1999 | Nguyen et al. |
| 5,971,965 A | 10/1999 | Mayer |
| 5,989,237 A | 11/1999 | Fowles et al. |
| 6,003,566 A | 12/1999 | Thibault et al. |
| 6,004,278 A | 12/1999 | Botich et al. |
| 6,063,068 A | 5/2000 | Fowles et al. |
| D427,308 S | 6/2000 | Zinger |
| 6,080,132 A | 6/2000 | Cole et al. |
| 6,090,093 A | 7/2000 | Thibault et al. |
| 6,099,511 A | 8/2000 | Devos et al. |
| 6,113,583 A | 9/2000 | Fowles et al. |
| 6,139,534 A | 10/2000 | Niedospial, Jr. et al. |
| 6,142,446 A | 11/2000 | Leinsing |
| 6,156,025 A | 12/2000 | Niedospial, Jr. et al. |
| 6,159,192 A | 12/2000 | Fowles et al. |
| 6,174,304 B1 | 1/2001 | Weston |
| 6,221,041 B1 | 4/2001 | Russo |
| 6,221,054 B1 | 4/2001 | Martin et al. |
| 6,238,372 B1 | 5/2001 | Zinger et al. |
| 6,245,044 B1 | 6/2001 | Daw et al. |
| D445,501 S | 7/2001 | Niedospial, Jr. |
| 6,258,078 B1 * | 7/2001 | Thilly ............ 604/411 |

| | | | | | | |
|---|---|---|---|---|---|---|
| 6,280,430 | B1 | 8/2001 | Neftel et al. | 7,799,009 B2 | 9/2010 | Niedospial, Jr. et al. |
| 6,343,629 | B1 | 2/2002 | Wessman et al. | 7,803,140 B2 | 9/2010 | Fangrow, Jr. |
| 6,348,044 | B1 | 2/2002 | Coletti et al. | 7,879,018 B2 | 2/2011 | Zinger et al. |
| 6,358,236 | B1 | 3/2002 | DeFoggi et al. | 2001/0029360 A1 | 10/2001 | Miyoshi et al. |
| 6,379,340 | B1 | 4/2002 | Zinger et al. | 2001/0051793 A1 | 12/2001 | Weston |
| 6,408,897 | B1 | 6/2002 | Laurent et al. | 2002/0017328 A1 | 2/2002 | Loo |
| 6,409,708 | B1 | 6/2002 | Wessman | 2002/0066715 A1* | 6/2002 | Niedospial, Jr. ............ 215/311 |
| 6,474,375 | B2 | 11/2002 | Spero et al. | 2002/0087118 A1 | 7/2002 | Reynolds et al. |
| 6,478,788 | B1 | 11/2002 | Aneas | 2002/0087141 A1 | 7/2002 | Zinger et al. |
| D468,015 | S | 12/2002 | Horppu | 2002/0087144 A1 | 7/2002 | Zinger et al. |
| 6,503,240 | B1 | 1/2003 | Niedospial, Jr. et al. | 2002/0121496 A1 | 9/2002 | Thiebault et al. |
| 6,503,244 | B2 | 1/2003 | Hayman | 2002/0123736 A1 | 9/2002 | Fowles et al. |
| 6,524,278 | B1 | 2/2003 | Campbell et al. | 2002/0127150 A1 | 9/2002 | Sasso |
| D472,316 | S | 3/2003 | Douglas et al. | 2002/0173752 A1 | 11/2002 | Polzin |
| 6,530,903 | B2 | 3/2003 | Wang et al. | 2003/0036725 A1 | 2/2003 | Lavi et al. |
| D472,630 | S | 4/2003 | Douglas et al. | 2003/0100866 A1 | 5/2003 | Reynolds |
| 6,544,246 | B1 | 4/2003 | Niedospial, Jr. | 2003/0120209 A1 | 6/2003 | Jensen et al. |
| 6,551,299 | B2 | 4/2003 | Miyoshi et al. | 2003/0153895 A1 | 8/2003 | Leinsing |
| 6,558,365 | B2 | 5/2003 | Zinger et al. | 2003/0195479 A1 | 10/2003 | Kuracina et al. |
| 6,581,593 | B1 | 6/2003 | Rubin et al. | 2003/0199846 A1 | 10/2003 | Fowles et al. |
| D483,487 | S | 12/2003 | Harding et al. | 2003/0199847 A1 | 10/2003 | Akerlund et al. |
| D483,869 | S | 12/2003 | Tran et al. | 2004/0044327 A1 | 3/2004 | Hasegawa |
| 6,656,433 | B2 | 12/2003 | Sasso | 2004/0073189 A1 | 4/2004 | Wyatt et al. |
| 6,666,852 | B2 | 12/2003 | Niedospial, Jr. | 2004/0153047 A1 | 8/2004 | Blank et al. |
| 6,681,810 | B2 | 1/2004 | Weston | 2004/0181192 A1 | 9/2004 | Cuppy |
| 6,681,946 | B1 | 1/2004 | Jansen et al. | 2004/0217315 A1 | 11/2004 | Doyle |
| 6,695,829 | B2* | 2/2004 | Hellstrom et al. ............ 604/415 | 2004/0236305 A1 | 11/2004 | Jansen et al. |
| 6,699,229 | B2 | 3/2004 | Zinger et al. | 2005/0124964 A1* | 6/2005 | Niedospial et al. ............ 604/411 |
| 6,715,520 | B2 | 4/2004 | Andreasson et al. | 2005/0137566 A1* | 6/2005 | Fowles et al. ............. 604/412 |
| 6,729,370 | B2 | 5/2004 | Norton et al. | 2005/0148994 A1 | 7/2005 | Leinsing |
| 6,736,798 | B2 | 5/2004 | Ohkubo et al. | 2006/0030832 A1 | 2/2006 | Niedospial et al. |
| 6,745,998 | B2 | 6/2004 | Doyle | 2006/0079834 A1 | 4/2006 | Tennican et al. |
| 6,752,180 | B2 | 6/2004 | Delay | 2006/0089603 A1 | 4/2006 | Truitt et al. |
| D495,416 | S | 8/2004 | Dimeo et al. | 2006/0106360 A1* | 5/2006 | Wong ............................ 604/411 |
| D496,457 | S | 9/2004 | Prais et al. | 2006/0135948 A1 | 6/2006 | Varma |
| 6,832,994 | B2 | 12/2004 | Niedospial, Jr. et al. | 2006/0253084 A1 | 11/2006 | Nordgren |
| 6,852,103 | B2 | 2/2005 | Fowles et al. | 2007/0060904 A1 | 3/2007 | Vedrine et al. |
| 6,875,203 | B1 | 4/2005 | Fowles et al. | 2007/0083164 A1 | 4/2007 | Barrelle et al. |
| 6,875,205 | B2 | 4/2005 | Leinsing | 2007/0088252 A1 | 4/2007 | Pestotnik et al. |
| 6,878,131 | B2 | 4/2005 | Novacek et al. | 2007/0088293 A1 | 4/2007 | Fangrow |
| 6,890,328 | B2 | 5/2005 | Fowles et al. | 2007/0088313 A1 | 4/2007 | Zinger et al. |
| 6,901,975 | B2 | 6/2005 | Aramata et al. | 2007/0106244 A1 | 5/2007 | Mosler et al. |
| 6,949,086 | B2 | 9/2005 | Ferguson et al. | 2007/0156112 A1 | 7/2007 | Walsh |
| RE38,996 | E | 2/2006 | Crawford et al. | 2007/0167904 A1 | 7/2007 | Zinger et al. |
| 6,997,917 | B2 | 2/2006 | Niedospial, Jr. et al. | 2007/0191760 A1 | 8/2007 | Iguchi et al. |
| 7,024,968 | B2 | 4/2006 | Raudabough et al. | 2007/0191764 A1 | 8/2007 | Zihlmann |
| 7,074,216 | B2 | 7/2006 | Fowles et al. | 2007/0191767 A1 | 8/2007 | Hennessy et al. |
| 7,083,600 | B2 | 8/2006 | Meloul | 2007/0219483 A1 | 9/2007 | Kitani et al. |
| 7,150,735 | B2 | 12/2006 | Hickle | 2007/0244461 A1* | 10/2007 | Fangrow ....................... 604/411 |
| 7,192,423 | B2 | 3/2007 | Wong | 2007/0244462 A1* | 10/2007 | Fangrow ....................... 604/411 |
| 7,294,122 | B2 | 11/2007 | Kubo et al. | 2007/0244463 A1* | 10/2007 | Warren et al. .................. 604/411 |
| D561,348 | S | 2/2008 | Zinger et al. | 2007/0255202 A1 | 11/2007 | Kitani et al. |
| 7,326,194 | B2 | 2/2008 | Zinger et al. | 2007/0265574 A1 | 11/2007 | Tennican et al. |
| 7,350,764 | B2 | 4/2008 | Raybuck | 2007/0265581 A1 | 11/2007 | Funamura et al. |
| 7,354,422 | B2 | 4/2008 | Riesenberger et al. | 2007/0270778 A9 | 11/2007 | Zinger et al. |
| 7,354,427 | B2 | 4/2008 | Fangrow | 2007/0287953 A1 | 12/2007 | Ziv et al. |
| 7,425,209 | B2 | 9/2008 | Fowles et al. | 2008/0009789 A1 | 1/2008 | Zinger et al. |
| 7,435,246 | B2 | 10/2008 | Zihlmann | 2008/0172024 A1 | 7/2008 | Yow |
| 7,452,348 | B2 | 11/2008 | Hasegawa | 2008/0249479 A1 | 10/2008 | Zinger et al. |
| 7,470,265 | B2 | 12/2008 | Brugger et al. | 2008/0312634 A1* | 12/2008 | Helmerson et al. ............ 604/414 |
| 7,488,297 | B2 | 2/2009 | Flaherty | 2009/0012492 A1 | 1/2009 | Zihlmann |
| 7,491,197 | B2 | 2/2009 | Jansen et al. | 2009/0054834 A1 | 2/2009 | Zinger et al. |
| 7,523,967 | B2 | 4/2009 | Steppe | 2009/0082750 A1 | 3/2009 | Denenburg et al. |
| D595,420 | S | 6/2009 | Suzuki et al. | 2009/0143758 A1* | 6/2009 | Okiyama ....................... 604/408 |
| D595,421 | S | 6/2009 | Suzuki et al. | 2009/0177177 A1 | 7/2009 | Zinger et al. |
| 7,540,865 | B2 | 6/2009 | Griffin et al. | 2009/0177178 A1* | 7/2009 | Pedersen ....................... 604/414 |
| D595,862 | S | 7/2009 | Suzuki et al. | 2009/0187140 A1 | 7/2009 | Racz |
| D595,863 | S | 7/2009 | Suzuki et al. | 2009/0299325 A1 | 12/2009 | Vedrine et al. |
| 7,611,487 | B2 | 11/2009 | Woehr et al. | 2009/0326506 A1* | 12/2009 | Hasegawa et al. ............ 604/406 |
| 7,611,502 | B2 | 11/2009 | Daly | 2010/0010443 A1 | 1/2010 | Morgan et al. |
| 7,632,261 | B2 | 12/2009 | Zinger et al. | 2010/0030181 A1 | 2/2010 | Helle et al. |
| 7,654,995 | B2* | 2/2010 | Warren et al. ................. 604/414 | 2010/0076397 A1 | 3/2010 | Reed et al. |
| 7,695,445 | B2 | 4/2010 | Yuki | 2010/0087786 A1 | 4/2010 | Zinger et al. |
| 7,722,090 | B2 | 5/2010 | Burton et al. | 2010/0228220 A1 | 9/2010 | Zinger et al. |
| D616,984 | S | 6/2010 | Gilboa | 2010/0312220 A1 | 12/2010 | Kalitzki |
| 7,731,678 | B2 | 6/2010 | Tennican et al. | | | |
| 7,743,799 | B2 | 6/2010 | Mosler et al. | | | |
| 7,758,082 | B2 | 7/2010 | Weigel et al. | DE | 4122476 A1 | 1/1993 |
| 7,771,383 | B2 | 8/2010 | Truitt et al. | DE | 19504413 A1 | 8/1996 |

FOREIGN PATENT DOCUMENTS

| | | | |
|---|---|---|---|
| DE | 202004012714 | U1 | 11/2004 |
| EP | 0192661 | A1 | 9/1986 |
| EP | 0195018 | A1 | 9/1986 |
| EP | 0258913 | A2 | 3/1988 |
| EP | 0416454 | A2 | 3/1991 |
| EP | 0518397 | A1 | 12/1992 |
| EP | 0521460 | A1 | 1/1993 |
| EP | 0637443 | A1 | 2/1995 |
| EP | 0806597 | A1 | 11/1997 |
| EP | 0814866 | A1 | 1/1998 |
| EP | 0898951 | A2 | 3/1999 |
| EP | 1008337 | A1 | 6/2000 |
| EP | 1029526 | A1 | 8/2000 |
| EP | 1051988 | A2 | 11/2000 |
| EP | 1329210 | A1 | 7/2003 |
| EP | 1454609 | A1 | 9/2004 |
| EP | 1454650 | A1 | 9/2004 |
| EP | 1498097 | A2 | 1/2005 |
| EP | 1872824 | A1 | 1/2008 |
| FR | 2029242 | A5 | 10/1970 |
| FR | 2869795 | A1 | 11/2005 |
| GB | 1444210 | A | 7/1976 |
| JP | 4329954 | A | 11/1992 |
| JP | 11503627 | T | 3/1999 |
| WO | 9403373 | A1 | 2/1994 |
| WO | 9507066 | A1 | 3/1995 |
| WO | 9600053 | A1 | 1/1996 |
| WO | 9629113 | A1 | 9/1996 |
| WO | 9832411 | A1 | 7/1998 |
| WO | 9837854 | A1 | 9/1998 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 0191693 | A2 | 12/2001 |
| WO | 0209797 | A1 | 2/2002 |
| WO | 03051423 | A2 | 6/2003 |
| WO | 2004041148 | A1 | 5/2004 |
| WO | 2005105014 | A2 | 11/2005 |
| WO | 2007015233 | A1 | 2/2007 |
| WO | 2007105221 | A1 | 9/2007 |
| WO | 2009029010 | A1 | 3/2009 |
| WO | 2009038860 | A2 | 3/2009 |
| WO | 2009040804 | A2 | 4/2009 |
| WO | 2009087572 | A1 | 7/2009 |
| WO | 2009093249 | A1 | 7/2009 |
| WO | 2009112489 | A1 | 9/2009 |

OTHER PUBLICATIONS

The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued Feb. 3, 2011 in Int'l Application No. PCT/IL2010/000777.
Int'l Search Report issued on Mar. 17, 2011 in Int'l Application No. PCT/IL2010/000854.
http://www.knovel.com/web/portal/browse/display?_EXT_KNOVEL_DISPLAY_bookid=1023&VerticalID=0 [retrieved on Feb. 9, 2011].
Int'l Search Report issued on Mar. 11, 2011 in Int'l Application No. PCT/IL2010/00915.
Office Action Issued May 12, 2011 in U.S. Appl. No. 12/063,176.
Grifols Vial Adapter Product Literature, 2 pages, Jan. 2002.
Novel Transfer, Mixing and Drug Delivery Systems, MOP Medimop Medical Projects Ltd. Catalog, 4 pages, Rev. 4, 2004.
Smart Site.RTM. Alaris Medical Systems Product Brochure, 4 pages, Issue 1, Oct. 1999.
Smart Site.RTM. Needle Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RTM. Valve, B. Braun Medical, Inc. website and product description, 3 pages, Feb. 2006.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/eu/en/products/Pages/Mixject.aspx.
http://www.westpharma.com/eu/SiteCollectionDocuments/Recon/mixject%20product%20sheet.pfg; Mixject product information sheet pp. 1.
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued in Int'l Application No. PCT/IL2005/000376.
Int'l Search Report Issued Aug. 25, 2008 in Int'l Application No. PCT/IL2008/000517.
Written Opinion of the ISR Issued in Int'l Application No. PCT/IL08/00517.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued in JP Application No. 2007-510229.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.

* cited by examiner

LIQUID DRUG DELIVERY DEVICES FOR USE WITH SYRINGES WITH WIDENED DISTAL TIPS

CROSS-REFERENCE TO RELATED APPLICATION

This application is a Section 371 of International Application No. PCT/IL08/001278, filed Sep. 24, 2008, which was published in the English language on Apr. 2, 2009, under International Publication No. WO 2009/040804 A2 and the disclosure of which is incorporated herein by reference.

FIELD OF THE INVENTION

The invention pertains to liquid drug delivery devices for use with syringes with widened distal tips for preventing a conventional needle with a female Luer connector being slidingly mounted thereon.

BACKGROUND OF THE INVENTION

Commonly owned PCT International Application No. PCT/IL2005/000376 entitled Liquid Drug Delivery Devices and Needle Shield Removal Device and published under PCT International Publication No. WO 2005/105014 illustrates and describes a liquid drug transfer device including a vial adapter with elastomer tubing for preparing a syringe having a widened distal tip with a reconstituted liquid drug for immediate administration to a subject (see WO 2005/105014's FIGS. 8 to 11). The widened distal tip is dimensioned to prevent a conventional needle being slidingly mounted thereon. The elastomer tubing's free end is intended to be sealingly stretched over a syringe's widened distal tip for effecting fluid communication between a syringe and a medical vial containing a medicament requiring reconstitution. Reconstitution typically requires agitation of the assemblage of the liquid drug transfer device, a vial and a syringe which may lead to inadvertent syringe detachment and contents spillage.

SUMMARY OF THE INVENTION

The present invention is directed toward liquid drug delivery devices for safely and securely preparing a syringe having a widened distal tip with a reconstituted liquid drug for immediate administration to a subject. The present invention is based on fluid control devices with rotationally detachable vial adapters as illustrated and described in commonly assigned U.S. Pat. No. 6,238,372 to Zinger et al.'s FIGS. 11 to 15 and include two modifications as follows: First, liquid drug delivery devices of the present invention include a syringe port with an elastomer sealing member for sealed fluid communication with a syringe with a widened distal tip and a single use locking mechanism for securing same to preclude inadvertent syringe detachment under normal use including agitation for reconstitution purposes. And second, liquid drug delivery devices of the present invention include a drug administration port with a widened distal tip preferably similar to a syringe's widened distal tip for the same purpose of preventing conventional needles with a female Luer connector being slidingly mounted thereon.

Syringe ports can include any suitable sealing arrangement for effecting sealed fluid communication with a syringe's widened distal tip. Suitable sealing arrangements include inter alia elastomer tubing for sealingly stretching over a syringe's widened distal tip similar to WO 2005/105014's liquid drug transfer device, an elastomer gasket against which a syringe's widened distal tip is sealingly urged thereagainst, and the like. The single use locking mechanisms preferably preclude inadvertent syringe detachment by the provision of one or more stopping members for snapping behind a syringe's widened distal tip to encircle its syringe tip. The single use locking mechanisms are preferably automatically actuated on sliding insertion of a syringe into a syringe port. Alternatively, single use locking mechanisms may require user actuation.

BRIEF DESCRIPTION OF THE DRAWINGS

In order to understand the invention and to see how it can be carried out in practice, preferred embodiments will now be described, by way of non-limiting examples only, with reference to the accompanying drawings, in which similar parts are likewise numbered, and in which.

DETAILED DESCRIPTION OF PREFERRED EMBODIMENTS OF THE PRESENT INVENTION

Figure 1A:
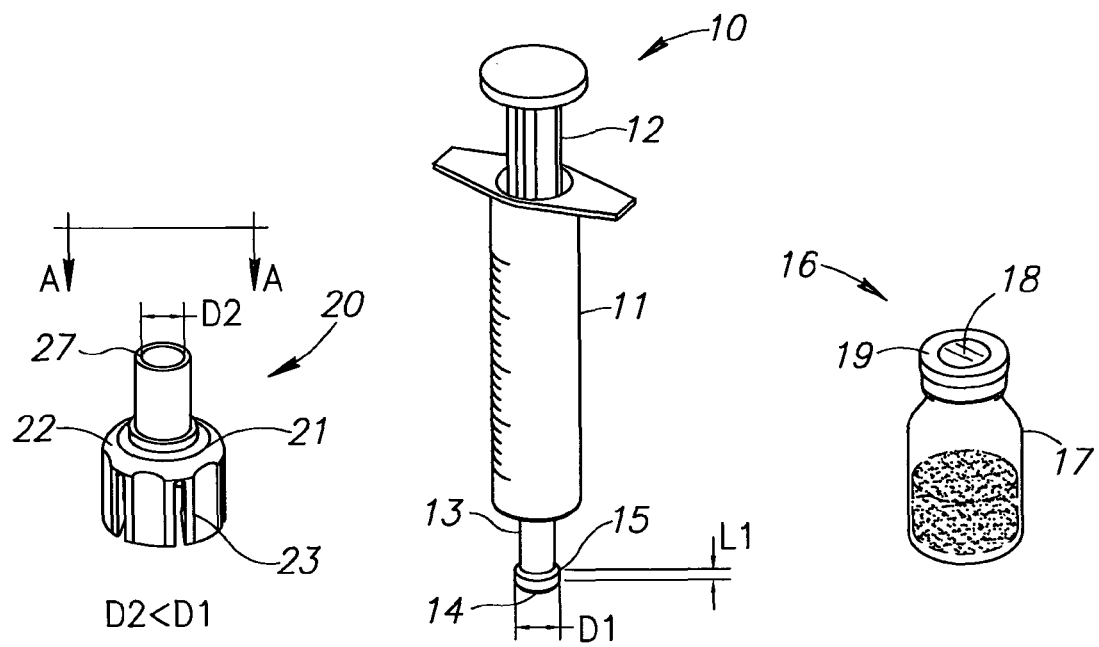
FIG. 1A corresponds to aforesaid commonly owned WO 2005/105014's FIG. 8 showing a liquid drug transfer device including a vial adapter with elastomer tubing for preparing a syringe with a reconstituted liquid drug for immediate administration to a subject.

FIG. 1A shows a syringe 10, a vial 16 and a liquid drug transfer device 20 for liquid drug reconstitution purposes. The syringe 10 includes a barrel 11 with a plunger 12 and a syringe tip 13 ending at a widened distal tip 14 for preventing the sliding mounting of a conventional needle with a female Luer connector thereon. The distal tip 14 has an outer diameter D1, a length L1 and an annular trailing surface 15. The syringe 10 typically includes a diluent for either reconstituting a powder drug or mixing with a liquid drug contained in the vial 16. The vial 16 includes an open topped bottle 17 sealed by a rubber stopper 18 capped by a metal band 19.

Figure 1B:
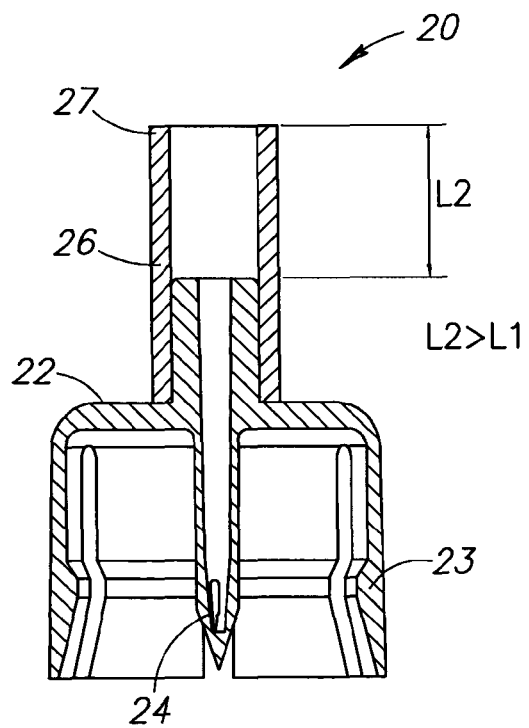
FIG. 1B corresponds to aforesaid commonly owned WO 2005/105014's FIG. 9 showing a longitudinal cross section of the liquid drug transfer device along line A-A in FIG. 1A.
Figure 2:
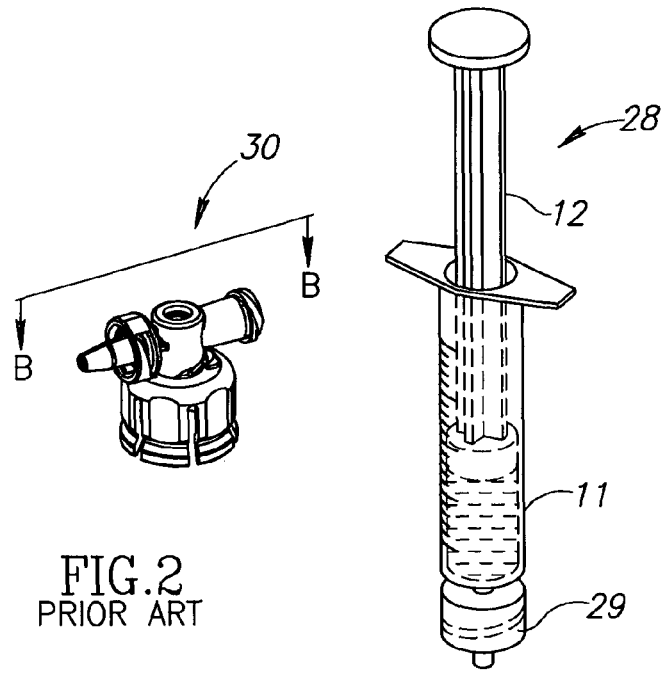
FIG. 2 is a pictorial representation of a syringe, a vial, and a fluid control device according to aforesaid commonly assigned U.S. Pat. No. 6,238,372's FIGS. 11 to 15.
Figure 3:
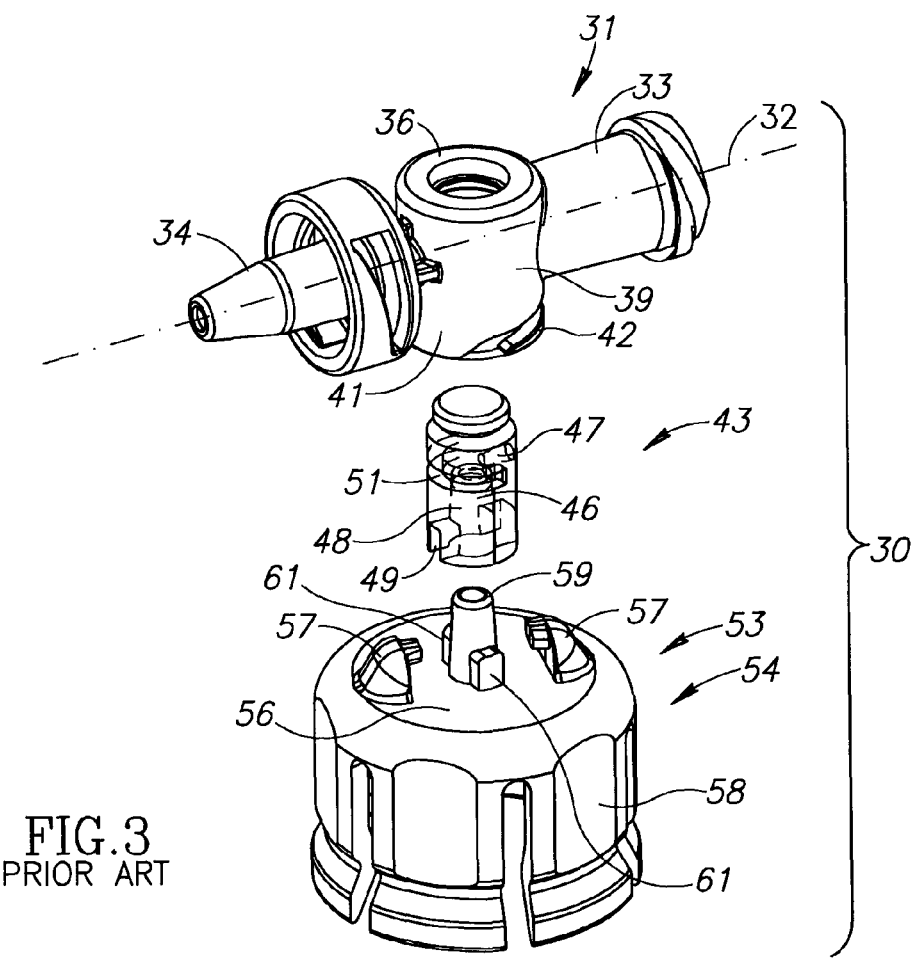
FIG. 3 is an exploded view of FIG. 2's fluid control device.

FIGS. 1A and 1B show the liquid drug transfer device 20 includes a vial adapter 21 with a top wall 22, a resiliently deformable slitted skirt 23 for snap fitting onto the vial 16, and a hollow puncturing member 24 for puncturing the vial's rubber stopper 18, and an elastomer tubing 26 in flow communication with the puncturing member 24. The tubing 26 has a distal end 27 for sealingly fitting over the distal tip 14 for enabling flow communication between the syringe 10 and the vial 16. The tubing 26 has an internal diameter D2 where D2<D1 and a free length L2 from its attachment point with the vial adapter 21 where L2>L1 for being sealingly stretched over preferably the entire distal tip 14 without tearing, ripping, and the like. The tubing 26 is preferably formed from one of the following substances: PVC, silicone, rubber, and the like.

FIGS. 2 to 5 show a conventional fluid control device 30 for use with a conventional syringe 28 with a male Luer lock connector 29 and a vial 16 for liquid drug reconstitution and administration purposes. The fluid control device 30 includes a housing 31 having a longitudinal axis 32, a syringe port 33 and a drug administration port 34 co-directional with the longitudinal axis 32, and a tubular vial adapter port 36 intermediate the syringe port 33 and the drug administration port 34. The syringe port 33 includes a lumen 37 in flow communication with the vial adapter port 36 and slidingly receiving the syringe 28. The drug administration port 34 includes a lumen 38 in flow communication with the vial adapter port 36 and intended for administrating a liquid drug.

The vial adapter port 36 has an outer cylindrical surface 39 with a lowermost portion 41 having a pair of opposite quarter turn screw threads 42. The vial adapter port 36 supports a flow control member 43 rotatable about an axis of rotation 44 generally perpendicular to the longitudinal axis 32. The flow control member 43 has an L-shaped mixing flow channel 46 including a radial section 47 for registration with the syringe port's lumen 37 in a mixing flow control position and an axial section 48 terminating in a diametrical slot 49. The flow control member 43 has a peripheral semi-circular administration flow channel 51 for registration with the syringe port's lumen 37 and the drug administration port's lumen 38 in an administration flow control position subsequent to a quarter turn with respect to its mixing flow control position.

The fluid control device 30 includes a vial adapter 53 with a skirt 54 for telescopically receiving a vial. The skirt 54 has a top surface 56 with a pair of opposite screw thread members 57 for screw thread engaging the screw threads 42 thereby coupling the vial adapter 53 to the housing 31, and six downward depending flex members 58 for snap fitting onto the vial 16. The vial adapter 53 includes an upright tapered hollow male connector 59 for sealing insertion into the flow control member's axial section 48 and a pair of keys 61 for insertion into the flow control member's slot 49 for coupling the vial adapter 53 to the flow control member 43. The vial adapter 53 includes a downward depending hollow cannula 62 for puncturing the vial's rubber stopper 18 and extending into a vial bottle's interior. The male connector 59 and the cannula 62 are in flow communication.

Figure 4:
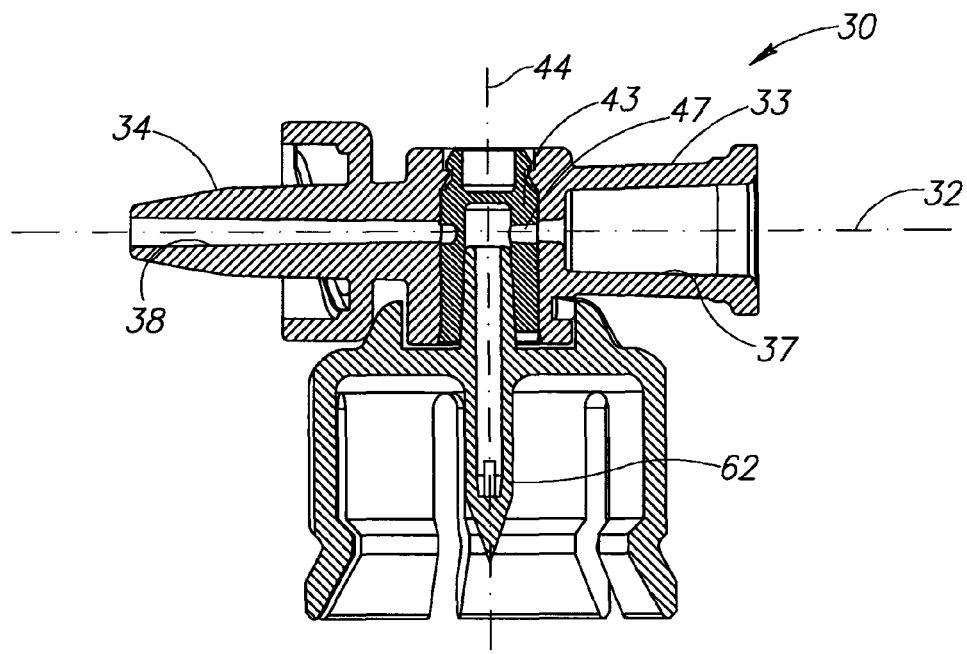
FIG. 4 is a longitudinal cross section of FIG. 2's fluid control device along line B-B in FIG. 2 in a reconstitution flow control position.
Figure 5:
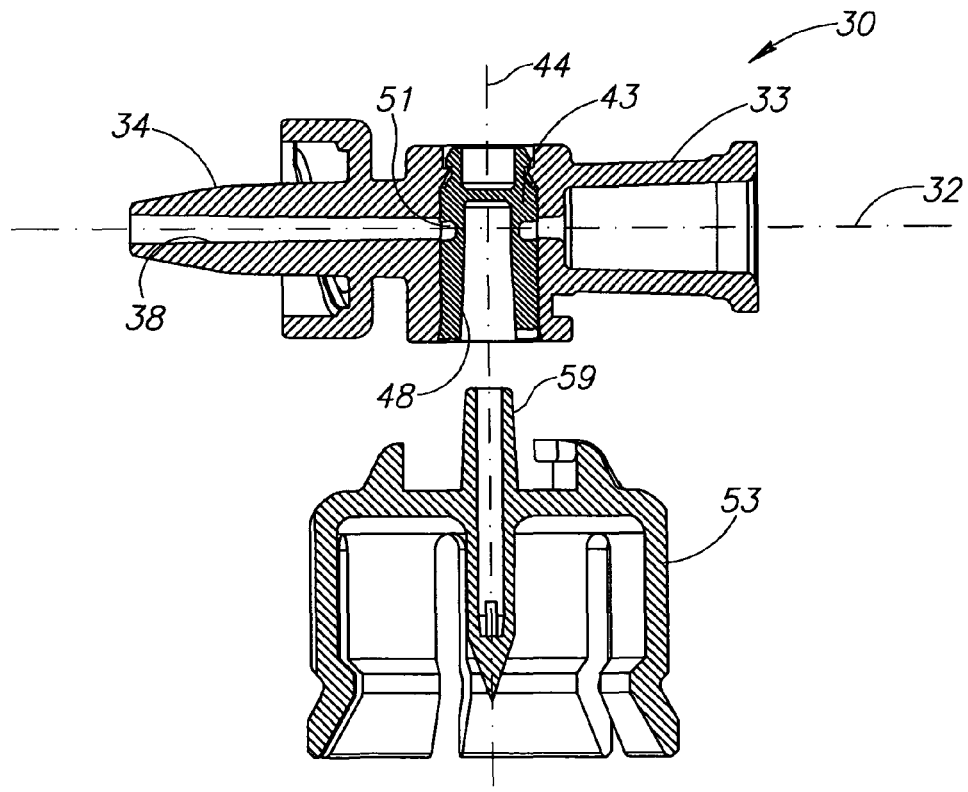
FIG. 5 is a longitudinal cross section of FIG. 2's fluid control device along line B-B in FIG. 2 in an administration flow control position subsequent to vial adapter detachment.

FIGS. 4 and 5 show the operation of the fluid control device 30:

FIG. 4 shows the fluid control device 30 with the vial adapter 53 coupled thereon and the flow control member 43 in its initial mixing flow control position enabling flow communication between a syringe inserted into the syringe port 33 and a vial inserted into the vial adapter 53. The diluent is injected into the vial for mixing with its contents prior to aspiration of the liquid drug into the syringe ready for administration.

FIG. 5 shows the fluid control device 30 subsequent to quarter turn rotation of the vial adapter 53 relative to the housing 31 for detaching the vial adapter 53 with a spent vial therefrom and simultaneously rotating the flow control member 43 from its initial mixing flow control position to its subsequent administration flow control position for enabling flow communication between the syringe port 33 and the drug administration port 34.

Figure 6:
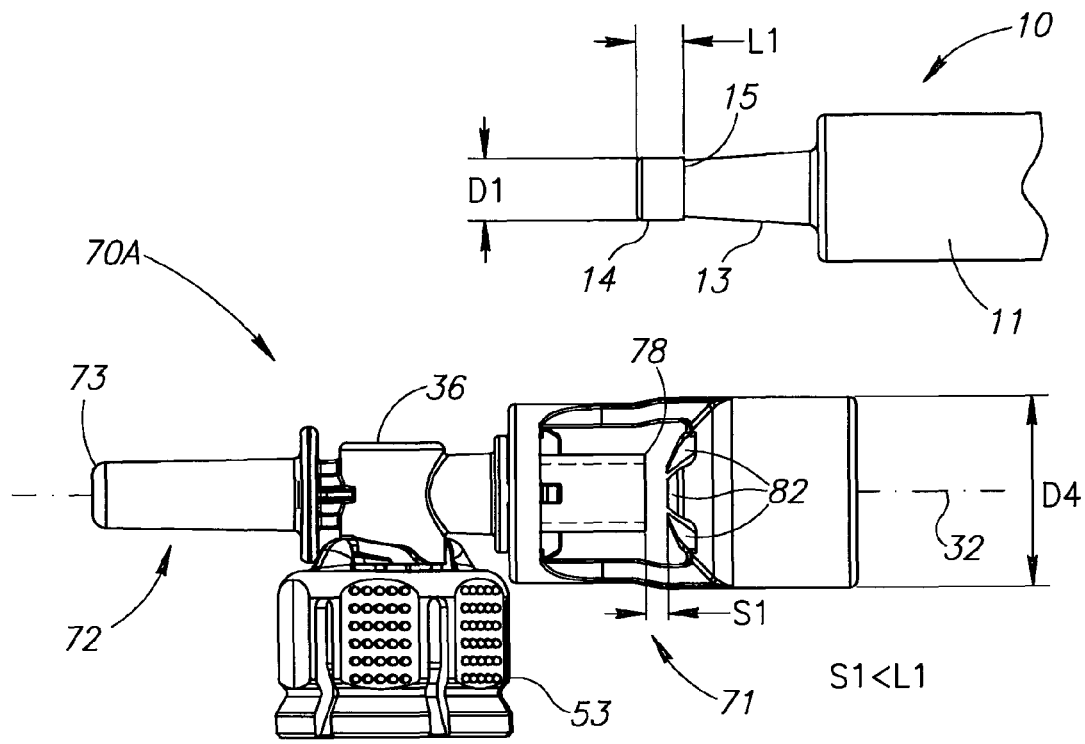
FIG. 6 is a side view of a first preferred embodiment of a liquid drug delivery device including a syringe port with elastomer tubing and an automatic single use locking mechanism in accordance with the present invention for use with a syringe having a widened distal tip for safely and securely preparing the syringe with a reconstituted liquid drug.
Figure 7:
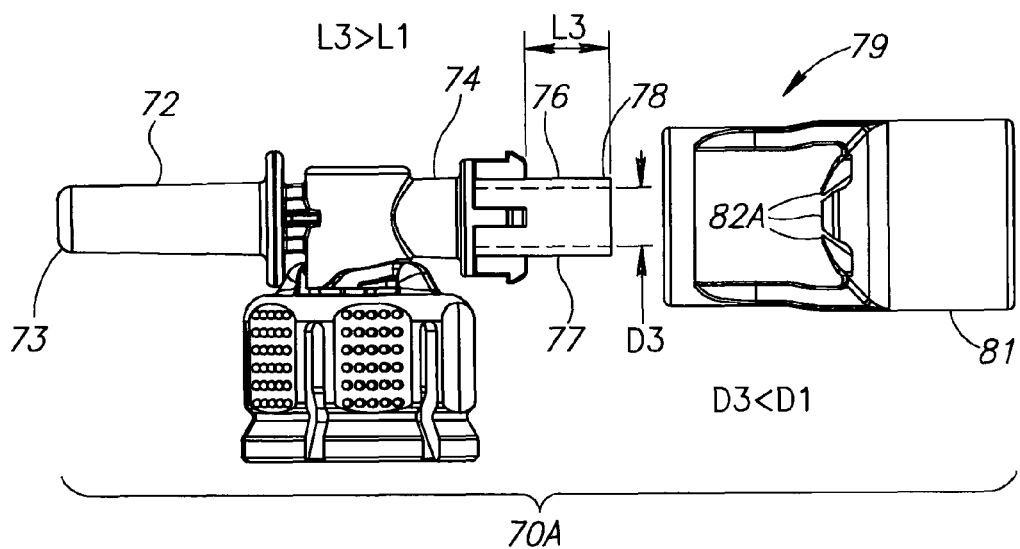
FIG. 7 is an exploded view of FIG. 6's syringe port.
Figure 8:
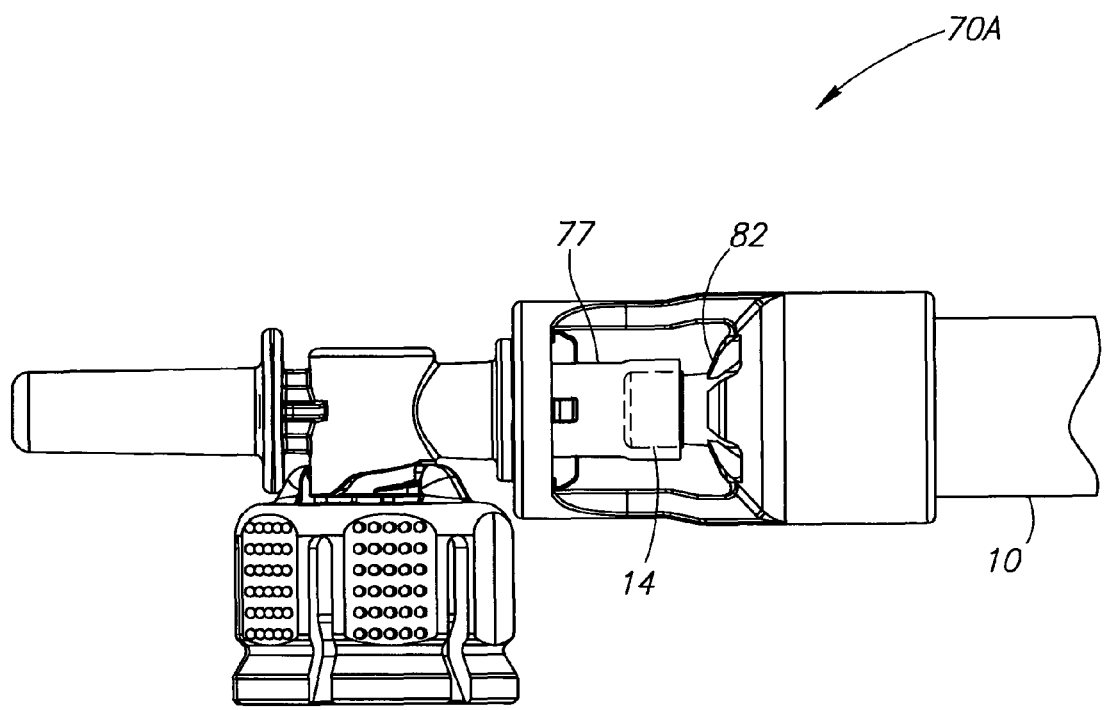
FIG. 8 is an assembled side view of FIG. 6's liquid drug delivery device and a syringe with a widened distal tip.

FIGS. 6 to 8 show a liquid drug delivery device 70A for use with a syringe 10 and a vial 16. The liquid drug delivery device 70A is similar in construction to the fluid control device 30 and therefore similar parts are likewise numbered. The two main differences between the device 70A and the device 30 are as follows: The device 70A includes a syringe port 71 designed to effect sealed fluid communication with a syringe 10 instead of a syringe 28. And second, the device 70A includes a drug administration port 72 having a widened distal tip 73 for preventing conventional needles with a female Luer connector being slidingly mounted thereon in a similar manner as the syringe 10.

The syringe port 71 includes an inlet port 74 provisioned with an elastomeric tubular sealing member 76 constituted by elastomer tubing 77 having a free end 78 and co-axial with the longitudinal axis 32. The tubing 77 is preferably formed from PVC, silicon, rubber, and the like. The tubing 77 has an inner diameter D3 and a free length L3 beyond its attachment point with the inlet port 74 where D3<D1 and L3>L1 for sealingly receiving the syringe's distal tip 14 on forced sliding insertion thereinto. The inlet port 74 supports an automatic single use locking mechanism 79 for precluding inadvertent syringe detachment. The locking mechanism 79 includes a solid tubular guide member 81 co-axial with the longitudinal axis 32 for assisting in user alignment of the syringe 10 along the longitudinal axis 32 for insertion into the syringe port but with an inner diameter D4 slightly larger than D1 such that the distal tip 14 can freely pass therethrough. The guide member 81 has four equispaced resiliently flexible stopping members 82 inwardly converging towards the vial adapter port 36 and terminating at stopping member tips 82A which stop short of the free end 78 by a separation S1 and define an aperture having a smaller diameter than the diameter D1 such that the syringe's distal tip 14 resiliently radially outwardly urges the stopping members 82 which snap behind same to encircle the syringe tip 13 on forced sliding insertion therethrough. Inadvertent detachment of the syringe 10 from the liquid drug delivery device 70A is prevented by the trailing surface 15 stopping against the stopping member tips 82A. The separation S1 is smaller than the length L1 for ensuring the distal tip 14 remains within the tubing 77 when the trailing surface 15 abuts against the stopping member tips 82A in the most rearward position of the syringe 10 with respect to the device 70A.

The use of the liquid drug delivery device 70A for safely and securely preparing a syringe 10 with a reconstituted liquid drug for immediate administration to a subject is similar to the use of the fluid control device 30.

The steps for using the liquid drug delivery device 70A are as follows: A user attaches a vial to the device's vial adapter. The user aligns a syringe along the device's longitudinal axis and subsequently inserts the syringe into its syringe port. The guide member supports the syringe as its widened distal tip outwardly radial urges the stopping members prior to stretching the elastomer tubing's free end. The user continues to slidingly insert the syringe until the stopping member tips snap behind the syringe's distal tip to secure the syringe therein and prevent outward syringe displacement. The syringe is sufficiently inserted into the elastomer tubing's free end to ensure sealed fluid communication therewith. The user injects the syringe's diluent into the vial and agitates the assemblage to reconstitute the vial's medicament. The user inverts the assemblage and aspirates the reconstituted liquid drug into the syringe. The user rotates the vial through a quarter turn to detach same. The device is now ready for immediate administration of the reconstituted liquid drug to a subject.

Figure 9:
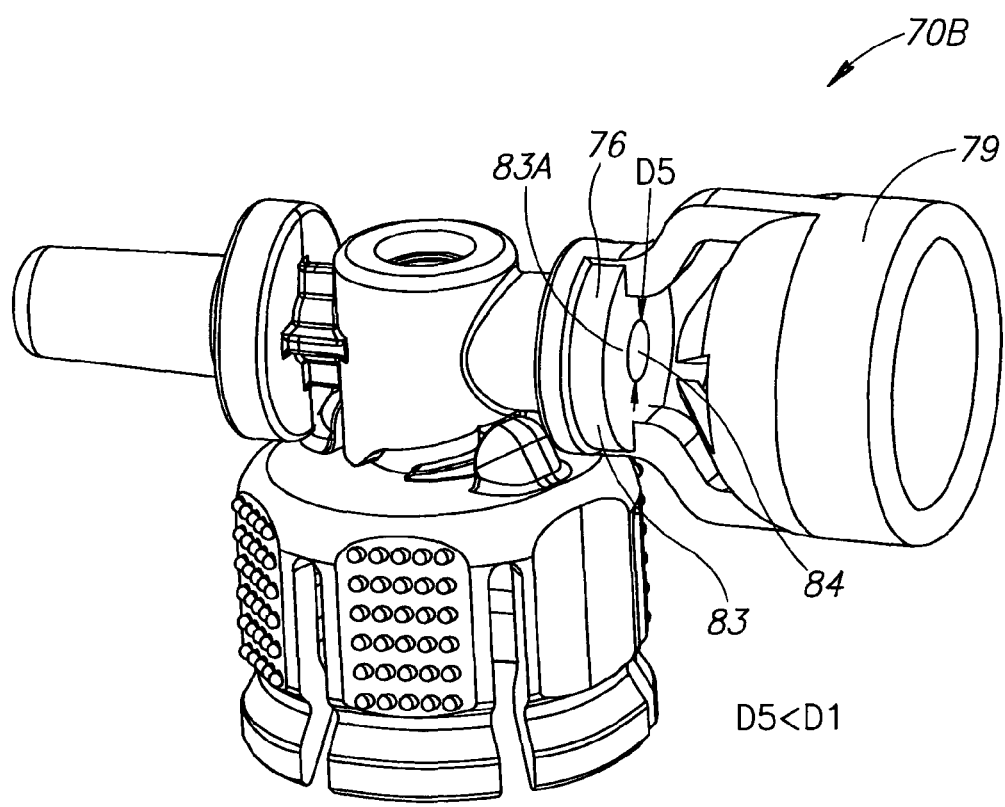
FIG. 9 is a perspective view of FIG. 6's liquid drug delivery device with a gasket instead of the elastomer tubing.
Figure 10:
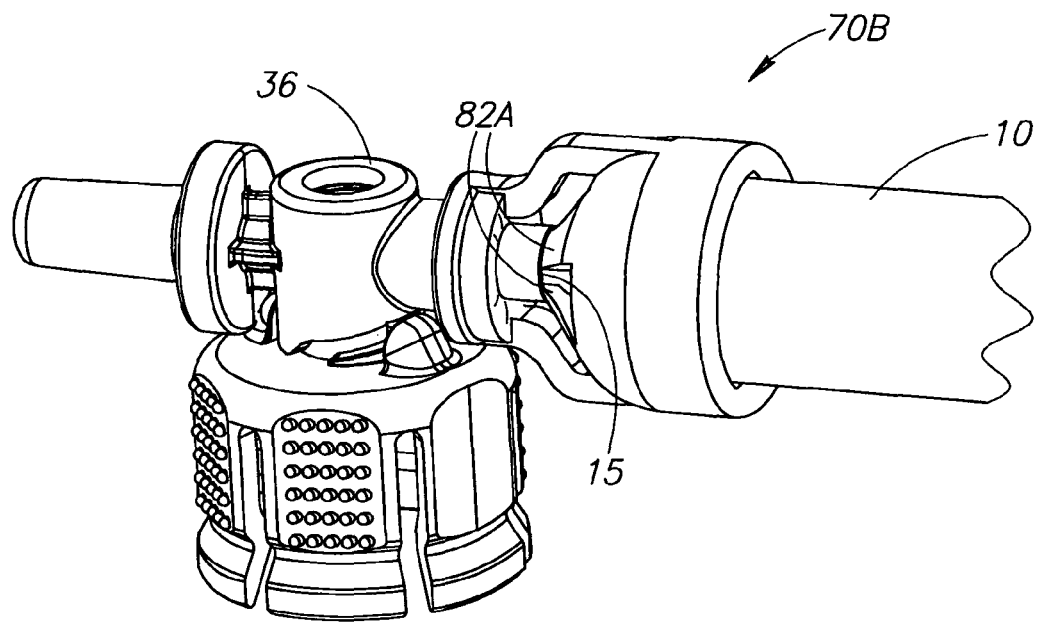
FIG. 10 is an assembled side view of FIG. 9's liquid drug delivery device and a syringe with a widened distal tip.

FIGS. 9 and 10 show a liquid drug delivery device 70B similar to the liquid drug delivery device 70A except that the elastomer tubular sealing member 76 is constituted by an annular gasket 83 instead of the tubing 77. The gasket 83 has an exposed front surface 83A and an axial throughgoing bore 84 of internal diameter D5 where D5<D1. The stopping member tips 82A stop short of the gasket's front surface 83A by a separation shorter than the length L1 such that the stopping member tips 82A continuously positively urge the trailing surface 15 towards the vial adapter port 36 whereby the distal tip 14 continuously slightly compresses the gasket 83 to effect a sealed fluid communication on forced sliding insertion of the syringe 10 into the syringe port 71 for effecting sealed fluid communication.

Figure 11:
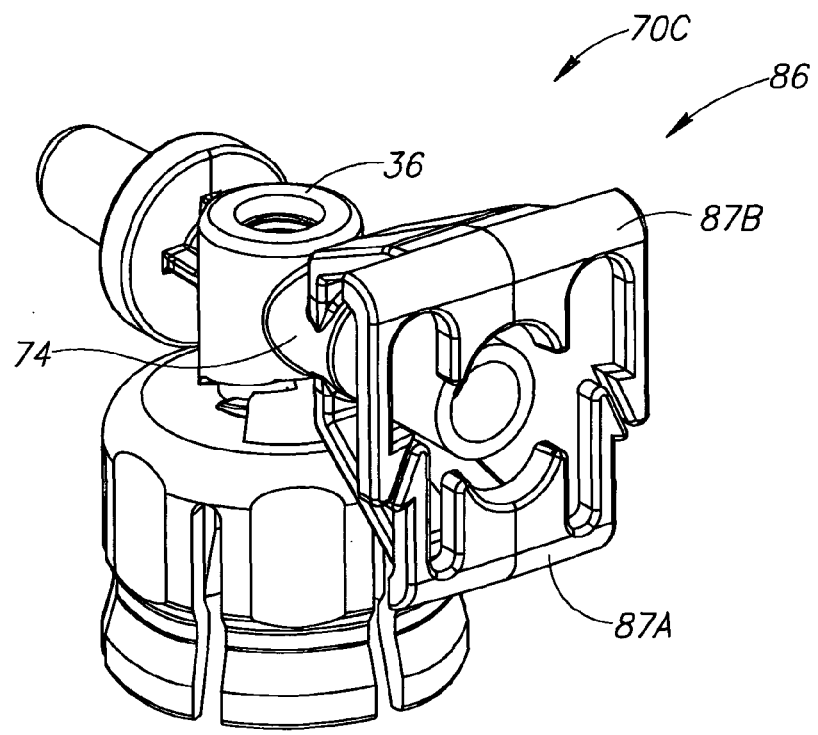
FIG. 11 is a perspective view of a second preferred embodiment of a liquid drug delivery device including a syringe port with elastomer tubing and a manual single use locking mechanism in accordance with the present invention.
Figure 12:
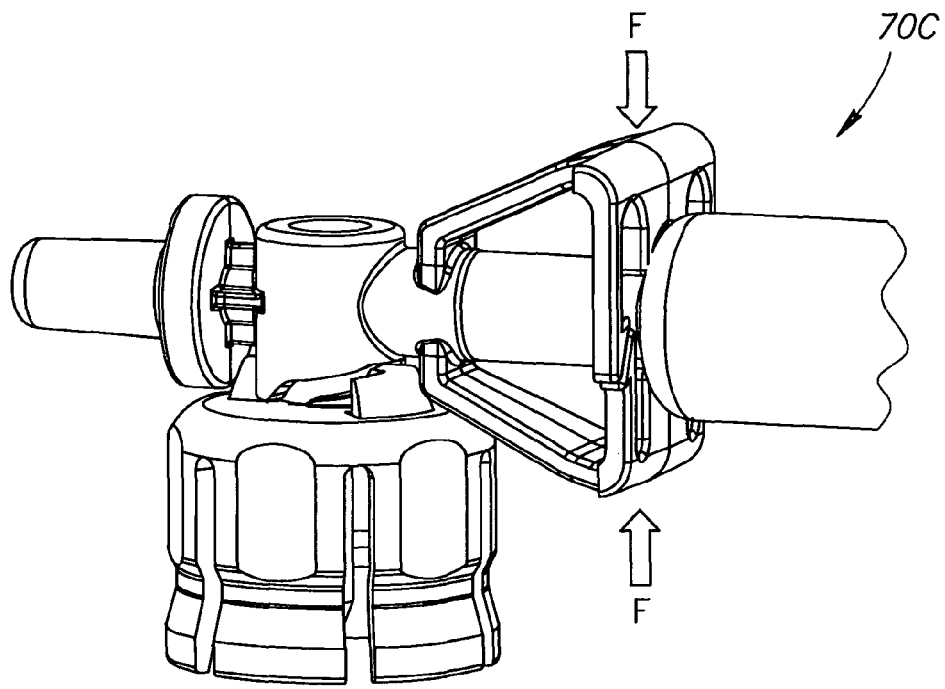
FIG. 12 is a perspective view showing manual actuation of FIG. 11's manual single use locking mechanism.

FIGS. 11 and 12 show a liquid drug delivery device 70C similar to the liquid drug delivery device 70A except that the inlet port 74 includes a manual single use locking mechanism 86 instead of the automatic single use locking mechanism 79. The manual single use locking mechanism 86 includes pivotally mounted male and female locking members 87A and 87B for a snap fit onto a syringe tip 13 behind its widened distal tip 14 on application of a manual compression force F directed towards the longitudinal axis 32.

Figure 13:
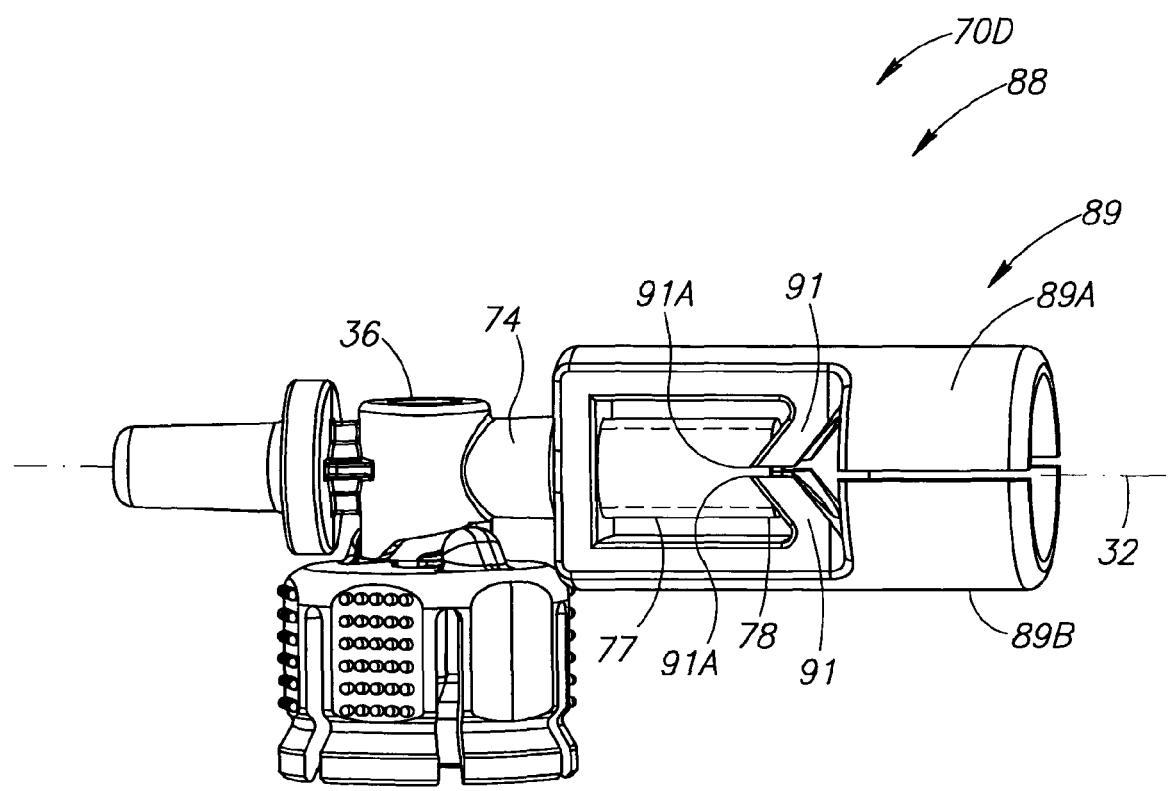
FIG. 13 is a perspective view of a third preferred embodiment of a liquid drug delivery device including a syringe port with elastomer tubing and an alternative automatic single use locking mechanism in accordance with the present invention.

FIG. 13 shows an alternative liquid drug delivery device 70D similar to the liquid drug delivery device 70A but its inlet port 74 includes a modified automatic single use locking mechanism 88. The locking mechanism 88 includes a split ring tubular guide member 89 co-axial with the longitudinal axis 32 and including opposite guide member elements 89A and 89B resiliently flexibly connected to the inlet port 74. The guide member 89 has an inner diameter which is greater than the diameter D1 such that the distal tip 14 can freely pass therethrough. The guide member 89 has a pair of opposite stopping members 91 inwardly converging towards the vial adapter port 36 and terminating at stopping member tips 91A stopping short of the free end 78 and defining an aperture having a smaller diameter than the distal tip 14's diameter D1 such that the syringe's distal tip 14 resiliently outwardly urges the stopping members 91 which snap behind same to encircle the syringe tip 13 on forced insertion therethrough. Inadvertent detachment of the syringe 10 from the liquid drug delivery device 70D is prevented by the trailing surface 15 stopping against the stopping member tips 91A. The distal tip 14 remains within the tubing 77 when the trailing surface 15 abuts against the stopping member tips 91A in the most rearward position of the syringe 10 with respect to the device 70D.

While the invention has been described with respect to a limited number of embodiments, it will be appreciated that many variations, modifications, and other applications of the invention can be made within the scope of the appended claims.

The invention claimed is:

1. A liquid drug delivery device for use with a syringe having a syringe tip ending at a widened distal tip having an outer diameter D1 and a length L1, and a medicinal vial with a rubber stopper, the device comprising:
   (a) a housing having a longitudinal axis, a syringe port and a drug administration port co-directional with said longitudinal axis for correspondingly receiving the syringe and administrating the liquid drug, and a tubular vial adapter port intermediate said syringe port and said drug administration port;
   (b) a flow control member rotatably supported in said vial adapter port about an axis of rotation generally perpendicular to said longitudinal axis, said flow control member including an L-shaped mixing flow channel with a radial section for flow communication with said syringe port in a mixing flow control position and an axial section, said flow control member including a peripheral semi-circular administration flow channel for enabling flow communication between said syringe port and said drug administration port in a subsequent administration flow control position,
   (c) a vial adapter for telescopically receiving a vial and including an upright tubular male connector and a downward depending tubular cannula for extending into the vial and in flow communication with said male connector,
   said vial adapter being initially coupled to said housing for sealing insertion of said male connector in said axial section and being rotationally detachable from said housing whereupon rotation of said vial adapter relative to said housing simultaneously rotates said flow control member from said mixing flow control position to said administration flow control position,
   characterized in
   said syringe port including an inlet port having an elastomeric tubular sealing member for sealed fluid communication with the syringe and a single use locking mechanism having at least two opposite stopping members for deployment behind the syringe's distal tip on insertion of the syringe into said syringe port thereby precluding inadvertent syringe detachment from said syringe port, and
   said drug administration port having a widened distal tip for preventing a conventional needle being slidingly mounted thereon.

2. The device according to claim 1 wherein said sealing member is constituted by elastomer tubing having an internal diameter D3 and a free length L3 beyond its attachment point with said inlet port where D3<D1 and L3>L1 for sealingly receiving the widened distal tip on forced sliding insertion of the syringe into said syringe port.

3. The device according to claim 1 wherein said sealing member is constituted by an annular elastomer gasket against which the widened distal tip is sealingly urged on sliding insertion of the syringe into said syringe port.

4. The device according to claim 1 wherein said locking mechanism includes a tubular guide member co-axial with said longitudinal axis for assisting in user alignment of the syringe therealong for facilitating insertion of the syringe into said syringe port,
   said tubular guide member having with at least two opposite stopping members inwardly converging towards said vial adapter port and terminating at stopping member tips stopping short of said sealing member and defining an aperture with a diameter smaller than the diameter D1 such that the syringe's widened distal tip resiliently radially outwardly urges said at least two stopping members which snap therebehind to encircle its syringe tip on forced insertion there through.

5. The device according to claim 4 wherein said locking mechanism includes a solid tubular guide member having at least two resiliently flexible stopping members.

6. The device according to claim 4 wherein said locking mechanism includes a split ring tubular guide member resiliently flexibly connected to said inlet port.

7. The device according to claim 1 wherein said locking mechanism includes a first locking member for snap fitting onto a second locking member on application of a manual compression force directed towards said longitudinal axis for encircling the syringe tip.

* * * * *